United States Patent [19]

Aurell et al.

[11] Patent Number: 5,312,745
[45] Date of Patent: May 17, 1994

[54] DETERMINATION OF COMPONENTS ACTIVE IN PROTEOLYSIS

[75] Inventors: Leif Aurell, Särö; Petter Friberger, Göteborg, both of Sweden

[73] Assignee: Chromogenix AB, Molndal, Sweden

[21] Appl. No.: 874,222

[22] Filed: Apr. 27, 1992

Related U.S. Application Data

[63] Continuation of Ser. No. 319,084, Feb. 16, 1989, abandoned.

[30] Foreign Application Priority Data

Jun. 18, 1987 [SE] Sweden ................................ 8702556

[51] Int. Cl.⁵ .......................... C12N 1/02; C12N 9/00; C12Q 1/37
[52] U.S. Cl. ...................................... 435/188; 435/23; 435/24; 435/183
[58] Field of Search ...................... 435/13, 23, 24, 183, 435/188

[56] References Cited

U.S. PATENT DOCUMENTS

| | | |
|---|---|---|
| 3,228,841 | 1/1966 | Cohen et al. ...................... 435/13 |
| 3,539,450 | 11/1970 | Demsch . |
| 4,334,018 | 12/1980 | Kirchhof .............................. 435/13 |
| 4,366,243 | 12/1982 | Rupchock et al. .................. 435/7 |
| 4,409,327 | 10/1983 | Bartl et al. . |
| 4,543,335 | 9/1985 | Sommer et al. . |
| 4,555,484 | 11/1985 | LaRossa et al. ..................... 435/21 |
| 4,563,420 | 1/1986 | Verheijen et al. . |
| 4,755,462 | 7/1988 | Schnabel ............................. 435/19 |
| 4,784,944 | 1/1988 | Kolde ................................... 435/13 |
| 4,990,445 | 2/1991 | Poudrier et al. .................... 435/22 |

FOREIGN PATENT DOCUMENTS

| | | | |
|---|---|---|---|
| 0014349 | 1/1980 | European Pat. Off. ...... | G01N 33/86 |
| 0168738 | 7/1985 | European Pat. Off. ....... | C12Q 1/38 |
| 3413311 | 10/1985 | Fed. Rep. of Germany ..... | C12Q 1/56 |

OTHER PUBLICATIONS

Kerr et al., Biochem 17, 2645-2648 (1978).

*Primary Examiner*—Christine M. Nucker
*Assistant Examiner*—M. P. Woodward
*Attorney, Agent, or Firm*—Pollock, Vande Sande & Priddy

[57] ABSTRACT

The invention relates to a freeze-dried reagent combination containing all reagents required for determination of components active in a proteolysis such as proteases and especially proenzymes, cofactors, inhibitors and activators for proteases which reagent combination is enclosed in a container such as a cuvette. The invention also relates to a new process for the preparation of such a reagent combination in which process the conditions are controlled so that all reagents can exist in one single solution which is freeze-dried without the reagent being deactivated; and the use of the reagent combination in the fields of coagulation and fibrinolysis.

11 Claims, 5 Drawing Sheets

DETERMINATION OF COMPONENTS ACTIVE IN PROTEOLYSIS

This application is a continuation of application Ser. No. 07/319,084 filed Feb. 16, 1989, now abandoned.

DESCRIPTION

1. Technical Field

This invention relates to a freeze-dried reagent combination, preferably for use in clinical diagnosis, which enables a simple and rapid determination of components active in proteolysis, for example proteases and especially proenzymes, inhibitors, cofactors and activators for proteases. The invention also concerns a new process for the preparation of such a reagent combination and use of this in the fields of coagulation and fibrinolysis.

2. Background Act

Protein-cleaving enzymes, so-called proteases, have a plurality of important functions in the body. As examples of proteases the following can be mentioned: Trypsin and chymotrypsin which are secreted from the pancreas and participate in the digestion process; elastase, kallikrein and catepsin of various types and the enzymes of the complementary system which i.a. participate in reactions caused by inflammatory and allergic conditions; thrombin and the factors $VII_a$, $X_a$, $XI_a$ and $XII_a$ consisting of proteases which participate in the chain of reactions leading to formation of blood coagulum, and plasmin and exogenic urokinase which are proteases providing the dissolution of the blood cagulum.

Thus, diagnostic methods for measurement in vitro of protease activity are of a great importance in a plurality of clinical applications. Not only the amount of active protease but first of all the amount of proenzyme that can be converted to an active protease, and also the amounts of inhibitors and activators participating in proeolytic processes are measured. Of course such measurements are of a great importance in investigations of pathological conditions. In certain treatments such as in surgery and/or medication, in many cases a determination of the quantities of certain of these substances is also first carried out.

Conventional methods for determination of components active in proteolysis, such as proteases and factors related thereto, for example proenzymes, inhibitors and activators, are based on so-called bioassays, immunologic reactions in vitro or utilization of biological proteins which proteins need not per se be natural substrates for the relative protease.

The disadvantages of the above methods are that they are time-consuming and laborious both in respect of performance and calibration, have a limited sensitivity and/or exhibit a lacking specificity and are also difficult to standardize.

In the last few years synthetic low molecular substrates have been developed based on amino acids or short peptides and provided with a usually photometrically, easily measurable marker which is easily split off by proteases. These substrates have to a large extent facilitated the methods of quantifying proteases as several of the disadvantages mentioned above have been eliminated by means of such substrates. (Hemker H.C.—Handbook of synthetic substrates, 1983, Martinus Nijhoff Publishers, Boston).

These substrates, especially such as are provided with a photometrically measurable marker, so-called chromogenic substrates, have thus enabled the development of methods having an improved specificity and reproducibility. Moreover, by these methods activity is measured instead of amount as, on the other hand, is the case with for example immunologic methods and, thus, a linear ratio of studied parameter to measuring result is obtained as distinguished from log-log- and lin-log ratios mostly occurring in so-called bioassays.

Despite the advantages indicated above measuring methods based on splitting of such, usually chromogenic, substrates are still impaired by several shortcomings limiting the usefulness thereof.

As a rule, these so-called substrate methods comprise two-step reactions which include, on one hand, a merely biochemical reaction and, on the other hand, a reaction between a protease and a suitable substrate. Depending on which active component is to be determined the reaction processes can be illustrated as follows.

A. Determination of inhibitor

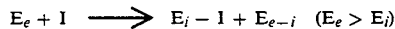

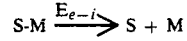

B. Determination of cofactor

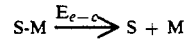

C. Determination of activator

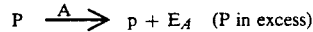

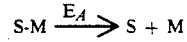

D. Determination of proenzyme

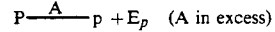

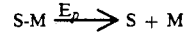

Thus, the second reaction step means splitting of a substrate having a marker through the influence of a corresponding enzyme, the amount of enzyme available for splitting consisting of the amount of active enzyme remaining after or being formed through the first reaction.

Thus, in all cases the amount of marker M released is proportional to the analytes I, C, A and P, respectively. The above abbreviations have the following meanings, concentrations being marked by index.

E = enzyme
I = inhibitor
S-M = substrate provided with marker
M = marker
S = substrate residue remaining after splitting off the marker
R = reactant reacting with the enzyme through the influence of a cofactor
C = cofactor
A = activator P=proenzyme or enzyme compound which can be otherwise activated P=residue from activation of a proenzyme/enzyme compound As a rule, these two-step methods are time-consuming and laborious. As a plurality of pipetting steps are included and it is essential that the reaction times of the respective step are followed with a great carefullness and skill is required, moreover, when carrying out the analyses. Furthermore, the two-step method will limit the number of tests that can be carried out manually in one and the same series.

Besides, the usefulness of the methods is impaired by comparatively short shelf life (one month or less) that, as a rule, reconstituted biochemical reagents have. Commercial reagents available at present for these analyses are usually packed so that there is enough for 20-200 analyses. Consequently the user should need, for economical reasons, to carry out a corresponding number of analyses within the time of the reconstituted reagents being stable. So far, technique and costs have not permitted simple packages for separate tests as included reagents usually must be packed individually in one way or other, as in separate packages or separate rooms in a packing container ("compartmentalized").

At present there is only one commercially available package form where the reagents for a single test are physically separated in one and the same plastic container (ACA ®, DuPont, USA). The container having a technically complicated design is merely useful in an instrument specially made for this purpose, that breaks the partitions between the reagent compartments automatically and adds samples and further reagents after preset times.

It is also possible to simplify handling of conventionally packed reagents to a certain extent by adapting reaction conditions and reactants so that the two-step process is converted to a one-step process. The two reactions are then allowed to proceed in parallel and in such a way that the analyte is still directly proportional to the photometer reading. This process is either carried out in such a way that several reagents are added immediately after one another—which does not reduce the number of pipetting steps—or that certain reagents are mixed (e.g. substrate and biochemical reagent) in advance. Pipetting is then facilitated but a still more unstable reagent (shelf life usually only one day) is obtained. Particularly the last-mentioned process has been used in automatic methods (see below).

One of the advantages of the substrate methods is their applicability to automatic analyzers for clinical use facilitating a change into a one-step method in the measuring process (Bergström K. and Lahnborg, G. Tromb. Res 1975, Vol. 6, 223-233; Kapke G. F. et al, Clin. Chem. 1982, Vol. 28, 1521-1524). In this way many of the disadvantages of the substrate methods are eliminated. However, an investment in automatic analyzers requires long test series and concentration on central units to become profitable, which means, however, that the period from sampling until the analysis results are obtained may become unacceptably long.

A comparatively complicated process of achieving one-step methods is described in EP-A2-0 168 738, pipetting steps and exact timing demands being avoided. However, the process described therein is substantially limited to the technically complicated method of applying to a fixed carrier matrix the necessary biochemical reagents and substrates either in separate processes using different solvents preventing reaction or by compartmentalizing. Moreover, an apparatus specially constructed for the purpose is required for reading the resulting color.

SUMMARY OF THE INVENTION

Thus, it is the object of this invention to provide a reagent combination by means of which determinations of proteolytically active components can be easily carried out in a single step using the substrate method, yet the disadvantages indicated above being eliminated.

This object is achieved according to the invention by means of a freeze-dried reagent combination.

Thus, the invention is related to a freeze-dried reagent combination enclosed in a container and intended for a direct or indirect determination of a component active in proteolysis through cleaving of a substrate included in the reagent combination and capable of being cleaved by a protease to produce a detectable response, characterized in that the reagent combination comprises all the reagents required for the determination each in a substantially unreacted form and optionally one or more additives known per se and is prepared by freeze-drying in a way known per se of a solution containing all the constituents included in the freeze-dried reagent combination each in a substantially unreacted form, said freeze-dried reagent combination having substantially its original activity at reconstitution e.g. in a buffer solution.

Best and Various Modes for Carrying Out Invention

The reagent combination is preferably enclosed in the container in an amount sufficient for carrying out one separate single-step substrate method determination of proteolytically active components, for example proenzymes, protease activators, cofactors or protease inhibitors or their activators.

Accordingly the present reagent combination contains a substrate that can be cleaved by a protease to produce a detectable response. Depending on which proteolytically active component is to be determined the reagent combination also contains other reagents, usually selected from the following components: Proenzyme, protease activator, protease inhibitor, an activator for the inhibitor and a cofactor for proteolysis. The reagent combination preferably also contains additives, for example stabilizing additives as is explained more in detail below.

Figure 1B:
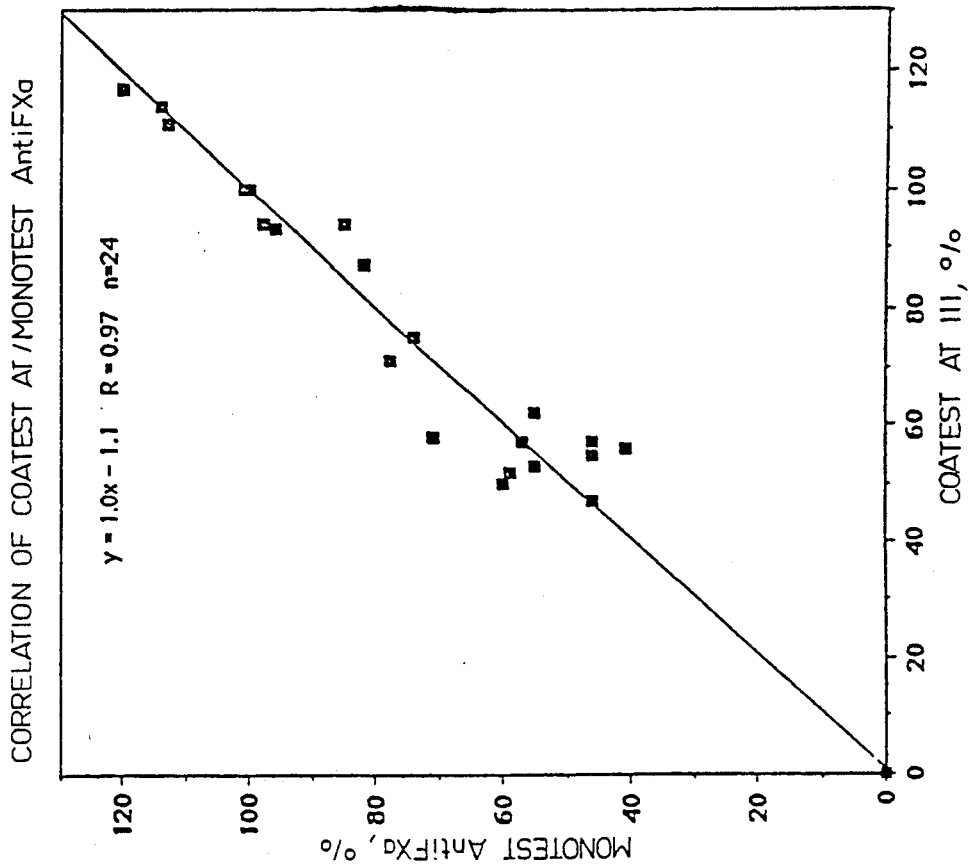
FIG. 1b illustrates the correlation to Coatest ® kit for determination of antithrombin.

Useful substrates are all substrates that can be split by proteases to produce a detectable response. Particularly suitable substrates are such as give a photometrically measurable response, so-called chromogenic substrates. The above-mentioned synthetic substrates are then preferably used. Such substrates are commercially available for example from KabiVitrum AB Diagnostika, Mölndal, Sweden, for example under the commercial designations S-2251 (H-D-Val-Leu-Lys-pNA.2HCl), S-2337 (Nα-benzoyl-Ile-Glu(γ-piperidide)-Gly-Arg-pNA.HCl), S-2366 (<Glu-Pro-Arg-pNA.HCl), S-2390 (H-D-Val-Phe-Lys-pNA.2HCl) and S-2732 (Nα-succinoyl-Ile-Glu-(γ-piperidide)-Gly-Arg-pNA.HCl). In addition to these substrates which are described in the following illustrative examples further examples of substrates are reported in Table I below which are useful according to the invention. However, the said substrates are only illustrative but not limitative of the present invention.

cofactor to be determined, c) a proenzyme or another activable enzyme compound and, respectively, d) an activator for the proenzyme. Embodiments of the invention preferred at present appear from the illustrative examples.

The present invention also relates to a process for preparation of the freeze-dried reagent combination.

More specifically, the invention relates to a process for preparation of the freeze-dried reagent combination, which process is characterized in that a solution containing all the reagents required for the determination and possibly one or more additives known per se is produced in a solvent such as water under conditions that are controlled in such a way that the reagents remain substantially unreactive in the resulting solution and in a subsequent freeze-drying of the solution; and that the solution is freeze-dried in the container in a way known per se, the freeze-dried reagent combination being obtained wherein the reagents are included in a substantially unreacted form and wherein the reagents have substantially original activity after reconstitution

TABLE I

| Analyte | Enzyme | Designation | Structure |
|---|---|---|---|
| 1. antifactor $X_a$ | F Xa | S-2767[x] | Boc—D—Arg—Gly—Arg-pNA |
| | | S-2775[x] | Succinoyl-D—Arg—Gly—Arg-pNA |
| | | CBS 31.39[xx] | $CH_3SO_2$—D—Leu—Gly—Arg-pNA |
| 2. Antithrombin | thrombin | S-2266[x] | H—D—Val—Leu—Arg-pNA |
| 3. antiplasmin | plasmin | S-2403[x] | <Glu—Phe—Lys-pNA |
| | | Chromozym-'L[xx] | Tosyl-Gly—Pro—Lys-pNA |
| 4. heparin | FXa | | see antifactor Xa! |
| 5. Fibrin monomer | plasmin | S-2466[x] | H—D—Glyn—Phe—Lys-pNA |
| | | PL-1[xx] | H—D—Nle—CHA—Lys-pNA |
| 6. t-PA | plasmin | S-2390[x] | H—D—Val—Phe—Lys-pNA |
| | | Chromozym-P'L[xx] | Tosyl-Gly—Pro—Lys-pNA |
| 7. FX | FXa | S-2732[x] | Succinoyl-Ile—Glu-(γ-piperidide)-Gly—Arg-pNA |
| | | S-2765[x] | Benzyloxycarbonyl-D—Arg—Gly—Arg-pNA |
| | | Spectrozyme Xa[xx] | Methyloxycarbonyl-D—CHG—Gly—Arg-pNA |
| 8. Plasminogen | plasmin | S-2406[x] | <Glu—Leu—Lys-pNA |
| | | Chromozym-PL[xx] | Tosyl-Gly—Pro—Lys-pNA |
| 9. Protein C | Protein $C_a$ | S-2288[x] | H—D—Ile—Pro—Arg-pNA |
| | | S-2401[x] | <Glu—Thr—Arg-pNA |

[x]Manufacturer KabiVitrum AB
[xx]Manufacturer Pentapharm AG, Basel, Schweiz
Abbreviations:
BO C = t-butyloxycarbonyl
CHA = cyclohexylalanin
CHG = cyclohexylglycin
Tosyl = p-toluene sulfonyl The invention is generally applicable to determination of proteolytically active components according to the basic principles for the substrate determination method provided such freeze-drying conditions can be established for a solution of the reagents under which conditions these components do not lose their activity, for example react with each other, but recover essentially their original activity after reconstitution.

So far it has been possible to establish suitable conditions for all reagent combinations of interest, especially in the fields of coagulation and fibrinolysis except the combination of reagents required for determination of $\alpha_1$-antitrypsin and F VIII. However, it is possible that such conditions possibly will be established also for these combinations after further experimentation.

The invention is well suited for determination of the proteolytically active components mentioned above for the substrate determination method. Thus, suitable reagent combinations are, when the proteolytically active component consists of a) an inhibitor, b) a cofactor, c) an activator or d) a proenzyme, a chromogenic substrate which can be split by protease in combination with a) a protease, b) a protease and a reactant which can react with the protease under the influence of the of the reagent combination, e.g. in a buffer solution.

It is essential according to the invention that all the reagents included in the freeze-dried combination are dissolved in the same solution at least in the very freeze-drying process. The process will be especially simple to carry out if a stock solution is first prepared from all reagents concerned under conditions controlled according to the invention, said stock solution also containing possible additives being thereafter distributed on containers and freeze-dried in these containers. However, it is of course also possible to prepare several stock solutions containing one or some of the reagents concerned and possible additives which solutions are thereafter brought together and freeze-dried simultaneously as one single solution in the respective container. Water is a suitable solvent even if additives of other solvents may be used, for example acetic acid, methanol and dimethyl sulfoxide.

According to a suitable embodiment of the invention such an amount of the solution (or solutions) is introduced into each container as is intended for one single test. A cuvette or a well in a microtiter plate or the like is then preferably used as container to which a sample can be added after which the container is directly transferred to a standard equipment for clinical analyses, for example for photometry.

According to the invention it is essential that the conditions in the preparation of the solution of all the reagents or in the combination of several solutions of reagents are adjusted, for example by providing the solvent with suitable additives of stabilizing soluble components and/or that the solvent is adjusted to such a pH-range, preferably by means of buffer salts, so that a mixture of such components usually reactive with each other can be dissolved in the preparation of the freeze-dried reagent combination without undesired but per se expected reactions taking place in the preparation. How the conditions are to be adjusted is dependent on the reagents included in the reagent combination and will be explained more in detail below.

The establishment of such controlled conditions has enabled a simultaneous freeze-drying according to the invention of all the reagents in one single solution. The mixture of reagents in the final form of the product is present in a freeze-dried state without any special compartmentalizing of the components included in the mixture which mixture has a good stability, an immediate dissolution of all the components included in the reagent mixture being achieved upon addition of a sample dissolved in a buffer for the freeze-dried reagent combination.

Thus, through the invention a product is provided which enables the utilization of all the advantages of the substrate determination methods and by which further advantages are achieved. For example, the need of several pipetting steps is eliminated as only pipetting for handling of the sample is required. Likewise the demands on accuracy as regards keeping correct incubation and reaction periods are eliminated. Moreover, lower demands are made on the technical skill of the operator and no specially constructed instrument for using the reagent combination is required for carrying out the analysis.

Another advantage of the products according to the invention is a considerably longer shelf life than for the corresponding reconstituted reagents and that they can be standardized by the manufacturer which provides a considerably simplified process for calculating the test result in comparison with previously known processes of the same type which usually require the establishment of a standard curve.

The present freeze-dried reagent combination is thus extremely well suited for routine use utilizing current instruments for carrying out single tests in small and/or big clinics when these have no automated analyzer in operation and/or no qualified personnel in service. Moreover, the product according to the invention provides the possibility of obtaining a quick response in acute situations as the determination can be carried out locally ("bedside") and as no preparative work such as preparation of reagent solutions, establishment of standard curve or running of controls is necessary.

Moreover, the use of the product according to the invention often means a considerable saving of resources and material in comparison with current products available on the market, such as "kits", which are not suited for determination of a few samples or in so far as they are designed for performance of a single analysis, said performance requiring special equipment.

As pointed out above the reagent combination of the invention contains a substrate capable of being cleaved by proteases and in addition other reagents depending on which proteolytically active component one wishes to determine. Thus, the preparation of this product must take place under conditions that are controlled with respect to which reagents are to be included in the reagent combination, i.e. depending on which active component is to be determined. The process is explained in the following more in detail with respect to embodiments thereof that are important at present, viz. determination of inhibitors, cofactors, activators and proenzymes.

I. Process for the Preparation of a Product for Determination of Inhibitors

Determination of the amount of protease inhibitor in a sample is based on the fact that a known and well-defined amount of an enzyme inhibited by the formation of 1:1-complex with the inhibitor is added to the sample and that the excess of enzyme is determined by addition of a known and well-defined amount of a suitable substrate.

According to the invention it has surprisingly been found that it is possible under conditions suited for production on a large scale to prepare a solution containing the enzyme as well as the substrate under conditions controlled in such a way that neither the enzyme nor the substrate is destroyed in the solution or in the process of freeze-drying. It is then extremely surprising that the enzyme does not react with the substrate in the preparation of the reagent combination although the enzyme and the substrate will achieve almost complete activity after reconstitution of the freeze-dried combination, for example by addition of a suitable buffer.

In determination of protease inhibitors the process of the invention is based on the fact that such a pH-range has been found within which the enzyme activity in respect of the substrate is negligible, however no denaturation of the enzyme or any hydrolysis of the substrate taking place. Such a range is preferably pH 3–5 and most preferably pH is 4.2. The optimum value within the range varies somewhat depending on which enzyme and which substrate are to be utilized in the process.

Furthermore, it is advantageous that such a buffer is utilized for adjustment of optimal pH, the salts of which leave at freeze-drying or are present after freeze-drying in such low amounts that the sample can be prepared before the analysis in currently used buffers having a pH of 6.5–9.5 so that optimal reaction conditions, i.e. pH 6.5–9.5, can be obtained for the substrate-enzyme reaction as well as for the enzyme-inhibitor reaction. Suitable buffers for the process of preparing reagents are weak organic acids such as formic acid or acetic acid mixed with the respective salt. Also other acids having a pKa-value in the same range such as citric acid, ascorbic acid etc. can be used but as a rule lower concentrations are required with the result that a considerably less stable pH is attained.

To avoid degradation processes during freeze-drying and during a following storage of the reagent mixture and in order to promote a rapid dissolution of the reagent mixture when adding the sample and minimizing reagent adsorption at the reagent container additives are suitably used, such as inorganic salts, inactive proteins, e.g. albumin, sugar, e.g. mannitol and/or surfactants such as polyethylene glycol (PEG, Carbowax® 8000 available from Union Carbide, USA) and Triton®
X-100 (Rohm & Haas, USA).

As shown in the following examples the excellent results obtained when using the reagent combination according to the invention are due to the fact that it is possible to find reaction conditions for the analysis, for example pH, ionic strength and buffer salts, which are appropriate for both the reactions, i.e. in the determination of inhibitor for the substrate-enzyme reaction as well as for the inhibitor-enzyme reaction.

The choice of substrate is also of a great importance when utilizing the present invention. Besides the fact that the substrate, as pointed out above, must be cleavable by protease to give a detectable response it is also essential that such a substrate is selected for a certain reaction as reacts effectively enough with the enzyme in order that reasonable measuring conditions, preferably reaction times shorter than 10 min, will be achieved but which is still not a substrate effective enough to prevent the enzyme molecule from reacting with the inhibitor. This condition can partly be expressed with the bonding ability of the substrate to the enzyme, $K_m$, which should preferably be $2-8\times10^{-4}$ mol/l.

Commercially available synthetic substrates are usually utilized, for example those indicated in table I and such as are described in the illustrative examples. Suitable substrate concentrations are $1-20\times10^{-4}$ mol/l. The concentration should be so high that there is a linear relationship between the enzyme concentration and the marker concentration. In general a preferred substrate concentration is $5\times10^{-4}$ mol/l.

However, it should be pointed out that an optimal substrate concentration and the affinity properties of the substrate are influenced by additives in the reaction mixture, and therefore strict general selection criteria cannot be defined.

Of course the choice of enzyme is dependent on which inhibitor is to be determined. Such enzymes are commercially available for a plurality of inhibitors of clinical interest, for example for several important protease inhibitors occurring in plasma such as antithrombin which can be determined via a reaction with thrombin or factor Xa in the presence of heparin, antiplasmin, which can be determined via plasmin, and kallikrein inhibitors, and according to the invention freeze-dried reagent combinations for carrying out these determinations can be prepared.

II. Process for the Preparation of a Product for Determination of Cofactors

Cofactors comprise many different types of substances actuating enzyme reactions. Here a factor is exemplified in the first place which actuates the inhibition of certain serine proteases, primarily $FX_a$ and thrombin, with the inhibitor antithrombin, viz. heparin. The method for determination of heparin and similar substances is similar to the inhibitor method described above except that the inhibitor, in this case antithrombin, must be added in excess.

Due to this the enzyme amount must be considerably increased in order that correct reaction conditions might be obtained. Otherwise the process is based on the same principles as the inhibitor method above exemplified for antithrombin and factor $X_a$. Thus, the same conditions apply as in the process for preparation of a reagent combination for inhibitor determination according to the process I.

Another cofactor that can be determined is fibrin monomer. This is a plasma protein converted by a coagulation enzyme and being a cofactor in the activation of the proenzyme plasminogen via the enzyme t-PA (plasminogen activator) which then serves as an activator. This enzyme i.e. the activator, is freeze-dried together with plasminogen, i.e. its substrate, and a chromogenic substrate suitable for the activation product, viz. the enzyme plasmin. The process for the preparation of the reagent combination corresponds to the process for preparation of a reagent combination for the inhibitor determination described above with the difference that the pH-range that can be used for the freeze-drying also comprises neutral pH and, thus, pH is suitably 3-8.5, and preferably 5-7.

III. Process for the Preparation of a Reagent Combination for Determination of Activators The method for determination of activator is built on the principle of freeze-drying a suitable proenzyme together with a substrate suitable for the activated proenzyme in the presence of additives promoting stability and solubility in analogy with what has been described above. Moreover, certain determination methods can require the presence of reaction promoting reagents. Thus, it is possible according to the invention to freeze-dry simultaneously all the reagents that are required for determination of for example t-PA, viz. plasminogen, plasmin substrate and stimulator of fibrin or polylysin type, and still maintain their activity, the conditions previously described being used which in analogy with the process II above also comprise neutral pH. Thus, a suitable pH-range is 3-8.5 and preferably 6-7.

IV. Process for the Preparation of a Reagent Combination for Determination of Proenzymes Proenzymes such as Protein C, plasminogen and factor X are well suited for determination by means of the substrate technique in the one-step embodiment provided the activator utilized as reagent in the presence of substrate for the corresponding activated proenzyme is fast-acting. Thus, the process according to this embodiment of the invention comprises freeze-drying of a substrate together with an activator that activates the major portion of proenzyme a occurring i the sample within some minute. The resulting reagent combination is intended for determination of proenzyme, the sample being diluted so much that inhibitors of the activated proenzyme occurring by nature in the sample are present in such a low concentration that these do not disturb the reaction between activated proenzyme and its substrate.

According to the invention freeze-drying is carried out in conventional manner, e.g. at 0.08-0.15 mbar by freezing at a temperature of $-45°$ to $-40°$ C., preferably $-42°$ C. for a time of 1-5 h, preferably 1 h, and a following drying for a time of 12-20 h, preferably 15 h, at a temperature of $12°-24°$ C., preferably $22°$ C.

The invention also relates to use of a freeze-dried reagent combination for quantitative, semi-quantitative or qualitative determination of coagulation factors and fibrinolysis factors in a sample, especially a biological one, such as whole blood, blood plasma, blood serum, cerebrospinal liquid, lung liquid or urine, in a one-step process by addition of the sample to the freeze-dried reagent combination enclosed in a container, preferably a cuvette, and reading in a way known per se of a response received.

The process according to the invention is explained in greater detail by means of the following examples, which are not limiting per se, with reference to the enclosed drawings, wherein FIGS. 1–9 show standard curves for a number of different components active in proteolysis and established at a wavelength of 405 nm by the aid of suitable freeze-dried reagent combinations according to the invention.

EXAMPLE 1

In this example a process for the preparation of a freeze-dried reagent combination for determination of a protease inhibitor, antifactor Xa and its use are described.

a) Acetate buffer, 1000 ml, is prepared by diluting 500 ml of a mixture of 0.2M acetic acid and 0.2M sodium acetate in water to 1000 ml by addition of distilled water. The desired pH-value of 4.2 is obtained with 368 ml 0.2M acetic acid and 132 ml 0.2M sodium acetate.

b) in order to obtain an improved stability and increased solubility of the reagent combination albumin and mannitol are added to the buffer solution a) in the amounts indicated below.

c) Preparation for freeze drying:

The substrate S-2732, 650 mg/l (0.8 mmol/l) and factor Xa, 1000 nkat (1000 nkat/l) are added to the buffer solution a), to which BSA, 5 g/l (0.5%) and mannitol, 10 g/l (1%) have been added.

d) Preparation of a freeze-dried reagent combination intended for determination of antifactor Xa: Each 200 μl of the solution c) is transferred to the respective microcuvette of plastic (Kartell Art. No. 1938). The cuvettes are placed in a freeze-drier at −42° C. for one hour and dried for 15 h at +22° C. and a pressure of 0.08–0.15 mbar.

e) Use of cuvettes d) for determination of antifactor Xa: 300 μl of plasma (diluted 1:500) in 0.05 mol/l Tris, pH 8.4, I=0.2 containing EDTA (7.5 mmol/l), heparin (3 IU/ml] and PEG (1%) are added to the cuvette d) containing the freeze-dried reagent combination consisting of S-2732 (0.13 mg) FXa (0.2 nkat) and BSA and mannitol.

After addition the pH of the test solution is 8.2. The reaction is allowed to take place at room temperature (25° C.) or at 37° C. and is interrupted after 8 min through addition of 300 μl 5% AcOH.

Figure 1A:
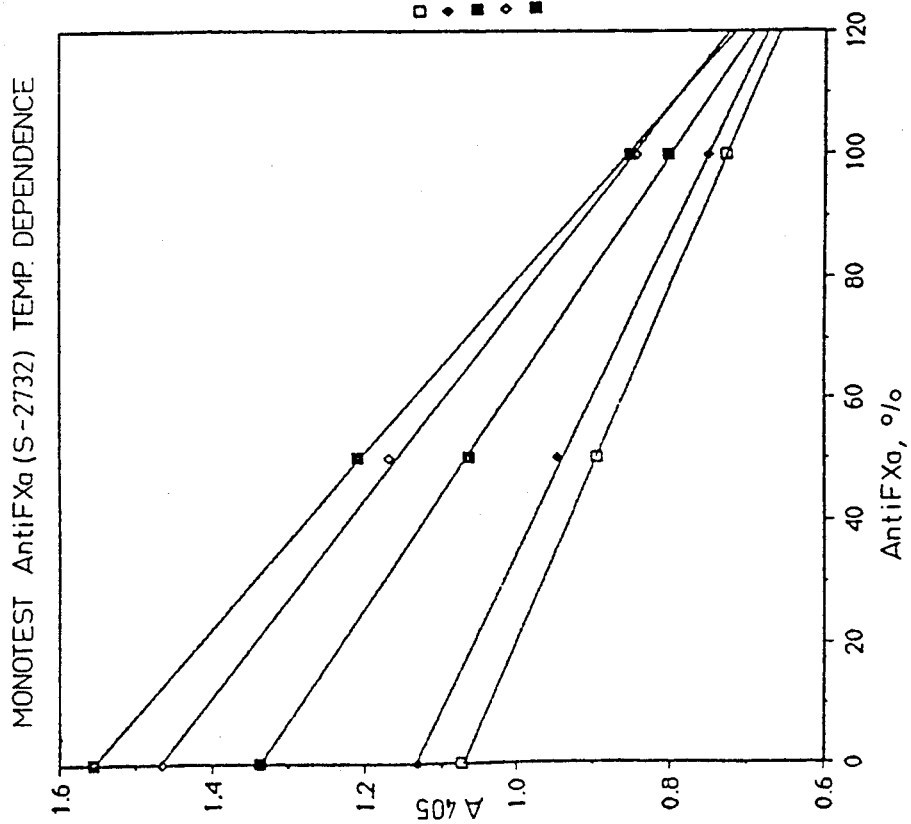
FIG. 1a illustrates curves of absorbance at 405 nm of samples containing antifactor Xa.
Figure 2:
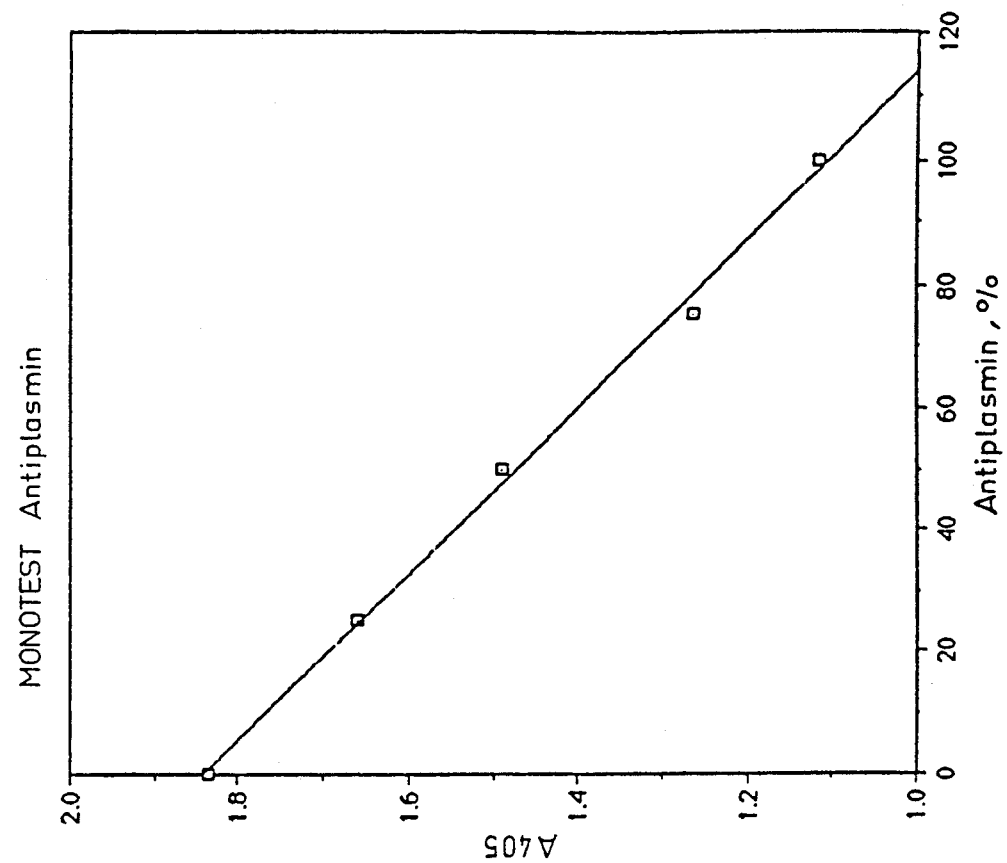
FIG. 2 illustrates a curve of absorbance at 405 nm for samples containing antithrombin.

The absorbance of the solution at 405 nm is thereafter read in a photometer and the result is compared with samples containing antifactor Xa in known amounts, by means of which the standard curves shown i FIG. 1a have already been prepared at the manufacturer of the reagent combination. This curves shows the relationship between dose and response and are the basis of factors calculated by the manufacturer and utilized by the user for calculation of the analyte in question.

The reaction was found to have a low temperature dependence which is also apparent from FIG. 1a.

The correlation to a generally used and commercially available "kit" for determination of antithrombin (Coates ® Antithrombin, KabiVitrum AB, Sweden) is shown in FIG. 1b.

EXAMPLE 2

In this example a process for the preparation of a reagent combination intended for determination of antithrombin and its use are described.

a) A freeze-dried reagent combination intended for determination of antithrombin and containing S-2366 (0.1 mg), thrombin (0.7 nkat) as well as BSA and mannitol is prepared in a cuvette in analogy with example 1.

b) Use of the reagent combination in determination of antithrombin. 300 μl plasma (diluted 1:80) in the same buffer as indicated in example 1e) is added to the cuvette from a), the contents of which being freeze-dried. The reaction is allowed to take place at 37° C. and interrupted after 8 min through addition of 300 μl of 5% acetic acid. Measuring is carried out in analogy with example 1e), the standard curve shown in FIG. 2 being obtained.

EXAMPLE 3

Figure 3:
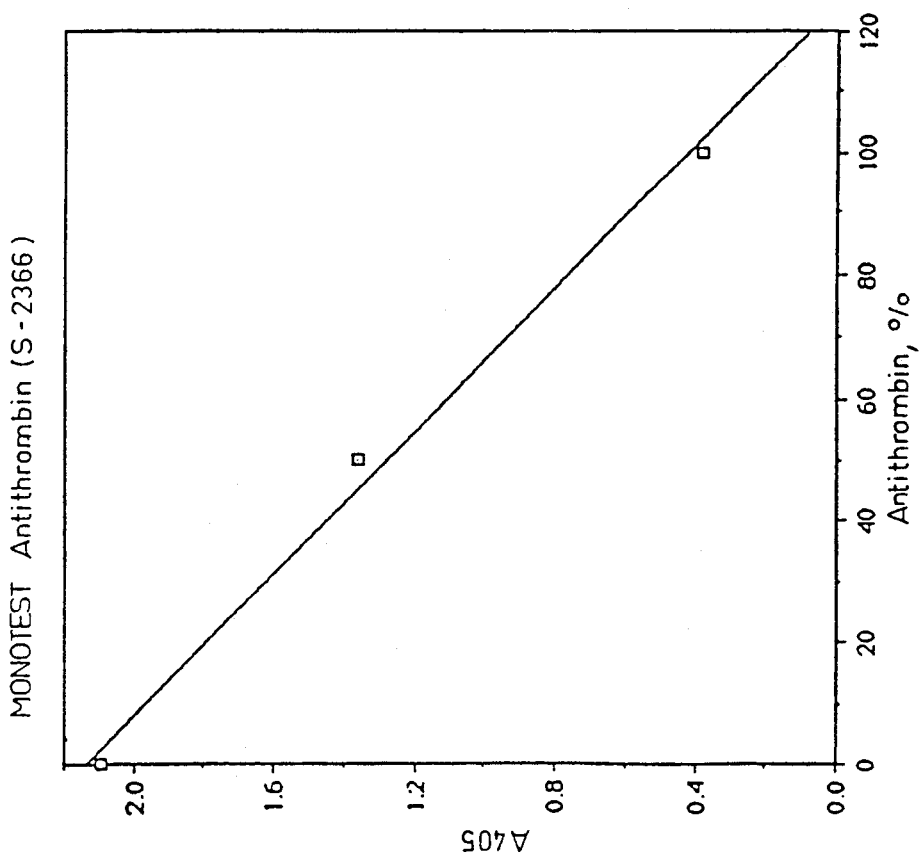
FIG. 3 illustrates a curve of absorbance at 405 nm for samples containing antiplasmin.

In this example a process for the preparation of a reagent combination intended for determination of antiplasmin and its use are described.

a) A cuvette containing a freeze-dried reagent combination intended for determination of antiplasmin and containing S-2251 (0.3 mg), plasmin (0.3 nkat) and BSA and mannitol is prepared in analogy with example 1.

b) Use of the reagent combination in determination of antiplasmin. 300 μl plasma (diluted 1:30) in 0.05 mol/l Tris, pH=8.3 comprising 0.15 mol/l methylamine is added to the cuvette from a), the contents of which being freeze-dried. The reaction takes place at 37° C. and is interrupted after 8 min by addition of 300 μl of 5% AcOH. Measurement is carried out in analogy with example 1e). The standard curve shown in FIG. 3 is obtained.

The above examples show reagent combinations intended for determination of protease inhibitors. The two immediately following examples illustrate reagent combinations intended for determination of cofactors.

EXAMPLE 4

Figure 4:
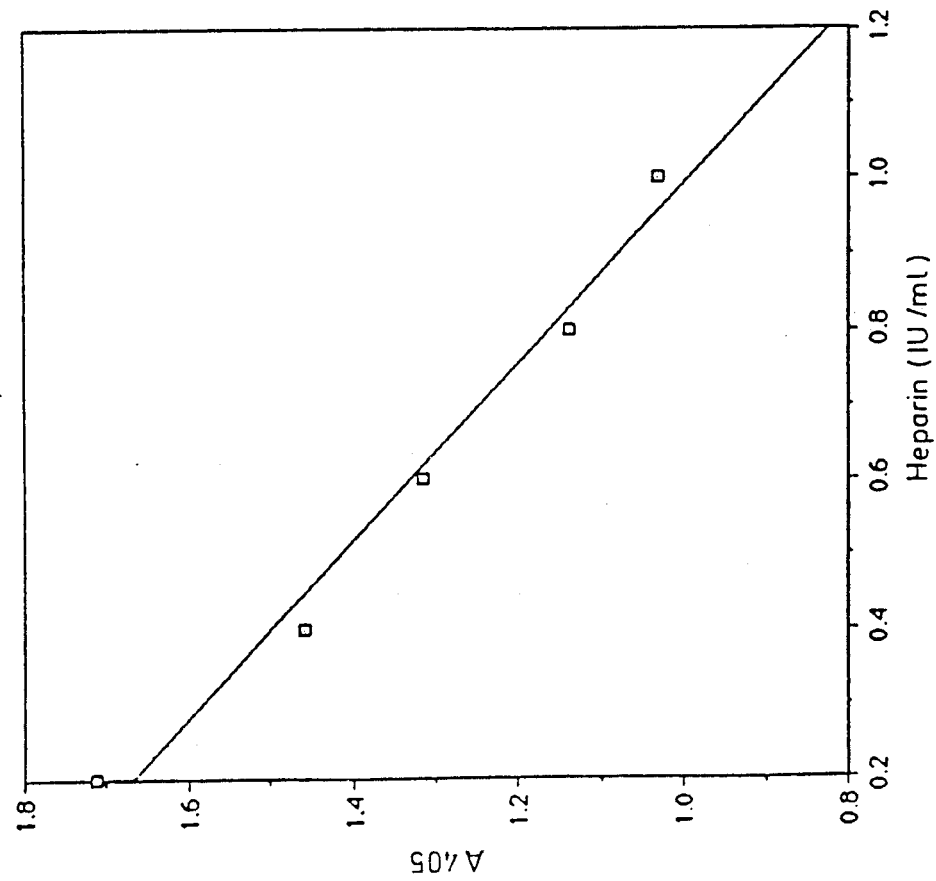
FIG. 4 illustrates a curve of absorbance at 405 nm for samples containing heparin.

A process for the preparation of a reagent combination for determination of heparin and its use are described in this example.

a) A cuvette comprising a reagent combination for determination of heparin and containing S-2732 (0.2 mg), FXa (0.5 nkat) and BSA and mannitol is prepared in analogy with example 1.

b) Use of the reagent combination in determination of heparin. 300 μl plasma (diluted 1:15) in 0.05 mol/l Tris, pH=8.4, I=0.2 containing EDTA (7.5 mmol/l) and PEG (1%) is added to the cuvette from a), the contents of which being freeze-dried. The reaction is carried out at room temperature and interrupted after 6 min through addition of 300 μl of 5% acetic acid. It is measured in analogy with example 1e). The standard curve shown in FIG. 4 is obtained.

EXAMPLE 5

In this example a process for the preparation of a reagent combination for determination of fibrin monomer and its use are described.

a) S-2390 (12 mg) and mannitol (19 mg) are dissolved in 7.0 ml 0.03 mol/l sodium acetate buffer, pH=4.9 containing 0.01% Tween$^R$ 80 and mixed with 2.5 mg human Glu-plasminogen dissolved in 0.8 ml sterile water. 100 mg BSA dissolved in 0.5 ml water and 3.6 μg t-PA dissolved in 0.8 ml sodium acetate buffer are added to the resulting solution after which additional buffer is added so that a total volume of 20 ml is achieved. Portions of 200 μl of the final solution are distributed on microcuvettes and freeze-dried according to example 1d).

b) Use of the reagent combination in determination of fibrin monomer.

Figure 5:
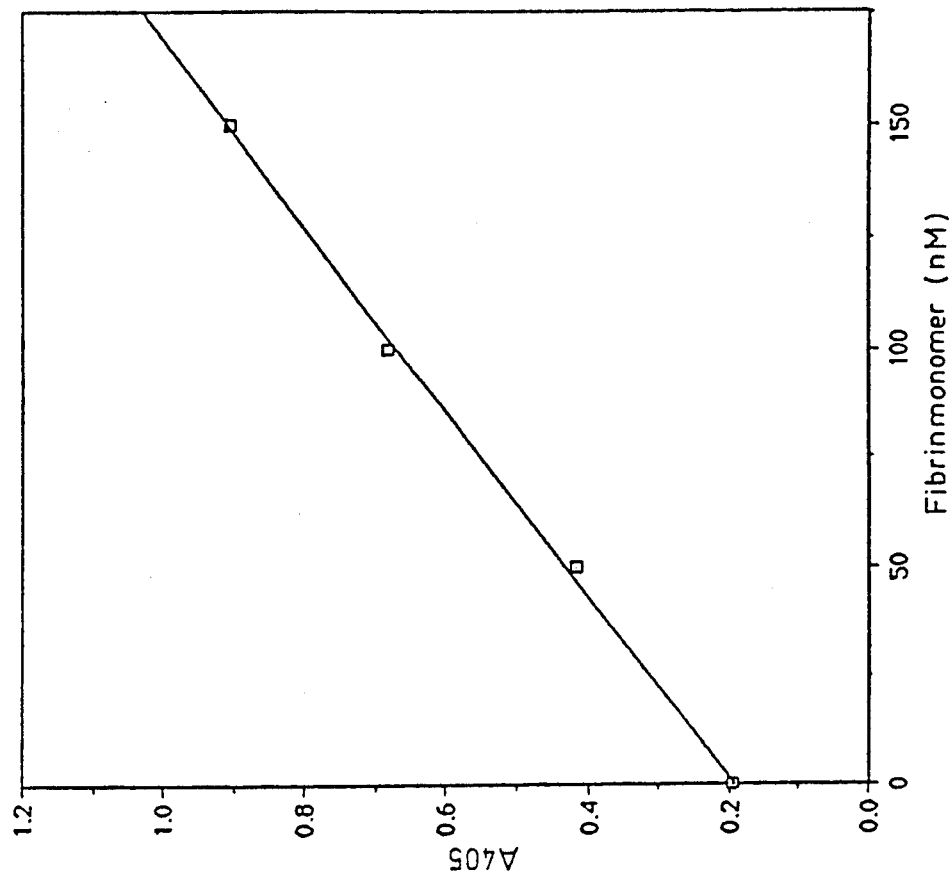
FIG. 5 illustrates a curve of absorbance at 405 nm for samples containing fibrinmonomer.

300 μl plasma (diluted 1:41) in 0.063 mol/l Tris, pH=8.5 containing 0.01% Tween ® 80 is added to the cuvette from a), the contents of which being freeze-dried and consisting of S-2390 (0.12 mg), plasminogen (25 μg) and t-PA (0.036 μg) as well as mannitol, Tween ® 80 and BSA. The reaction takes place at room temperature and is interrupted after 20 min by addition of 300 μl of 20% acetic acid. It is measured in analogy with example 1e). The standard curve shown in FIG. 5 is obtained.

An embodiment intended for determination of an activator for an enzyme reaction is illustrated in the following example.

EXAMPLE 6

A process for the preparation of a reagent combination for determination of t-PA and its use are described in this example.

a) S-2251 (9 mg) dissolved in 13.5 ml distilled water is mixed with 0.75 ml of an aqueous solution containing plasminogen (18.75 CU) and mannitol (15 mg). The resulting solution is cooled and mixed with 0.75 ml of an aqueous solution containing CNBr-digested fibrin(o-gen) (3.75 mg) and mannitol (15 mg). Portions of 200 μl of the final solution are distributed on microcuvettes and freeze-dried according to example 1d).

b) Use of the reagent combination in determination of t-PA.

300 μl of pretreated plasma (diluted 1:125) in 0.05 mol/l Tris, pH=8.3 containing 0.01% Tween ® 80 is added to the cuvette from a), the contents of which being freeze-dried and consisting of S-2251 (120 μg), plasminogen (0.25 CU) and CNBr-digested fibrin(ogen) (50 μg) as well as mannitol. The reaction is allowed to take place at 37° C. and interrupted after 2 h and 45 min through addition of 300 μl 20% AcOH.

Figure 6:
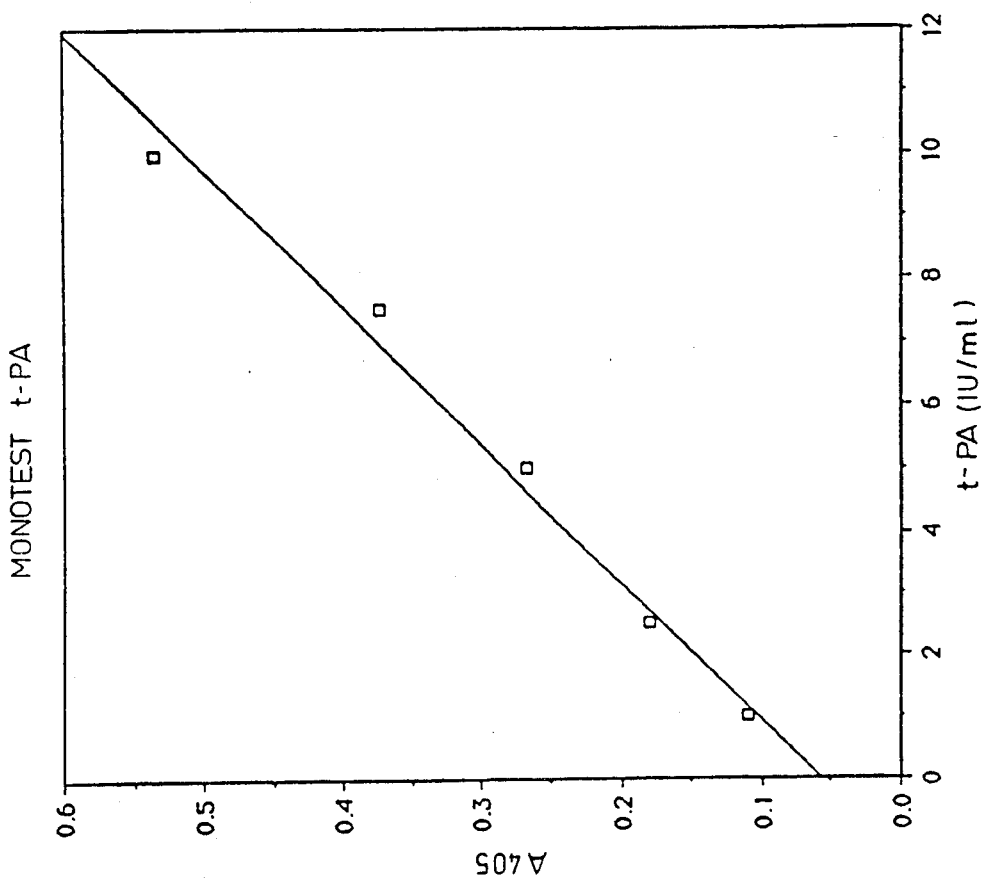
FIG. 6 illustrates a curve of absorbance at 405 nm for samples containing t-PA.

It is measured in analogy with example 1e) and the standard curve shown in FIG. 6 is obtained.

Embodiments intended for determination of proenzymes are illustrated in the following example.

EXAMPLE 7

A process for the preparation of a reagent combination for determination of factor X and its use are described in this example.

a) S-2337 (24 mg) and mannitol (120 mg) dissolved in 6.5 ml of distilled water are mixed with 3.5 ml of an aqueous solution containing Russel's Viper Venom (RVV, Miami Serpentarium Labs, USA) (0.9 mg) and NaCl (60 mg). A solution of $CaCl_2$ (0.1 mol/l) is added to the resulting solution so that a total volume of 20 ml is obtained. Portions of 200 μl of the final solution are distributed on microcuvettes and freeze-dried according to example 1d).

b) Use of the reagent combination in determination of factor X.

Figure 7:
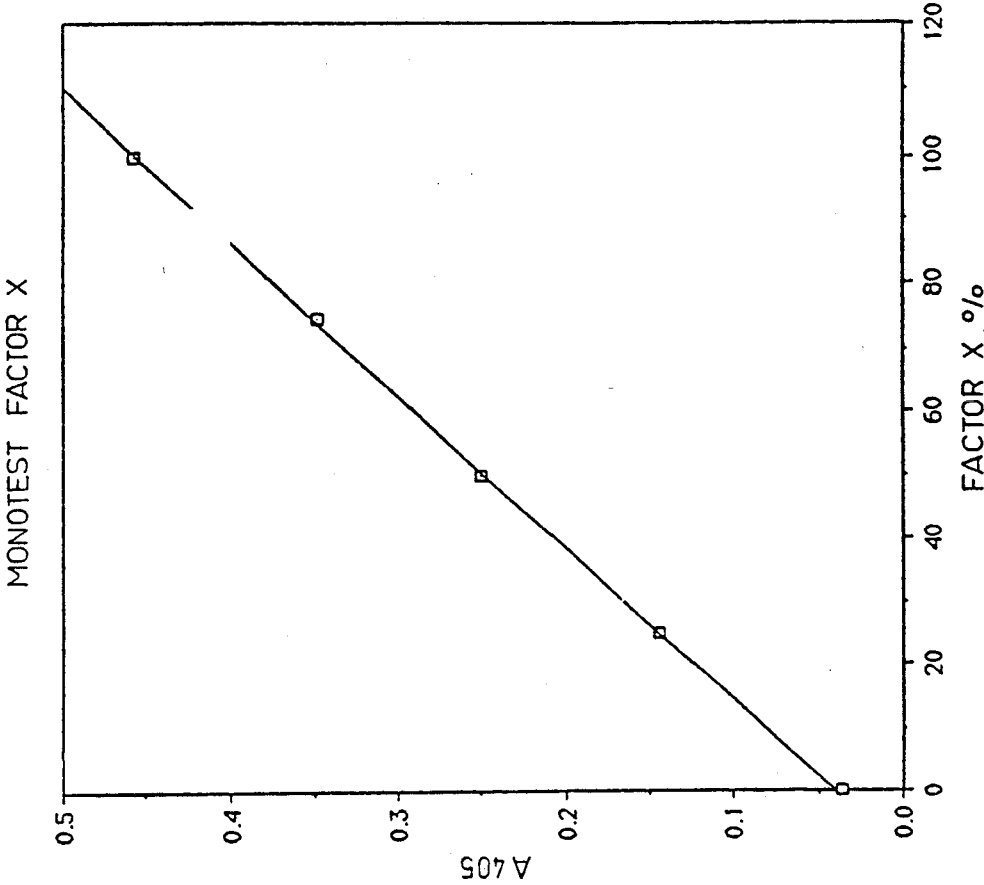
FIG. 7 illustrates a curve of absorbance at 405 nm for samples containing Factor X.

600 μl of plasma (diluted 1:60) in 0.05 mol/l Tris, pH=7.8 containing Polybrene ® (20 mg/l, Aldrich, USA) are added to the cuvette from a), the contents of which being freeze-dried and consisting of S-2337 (0.24 mg) and RVV (9 μg) as well as mannitol, $CaCl_2$ and NaCl. The reaction takes place at 37° C. and is interrupted after 3 min. through addition of 200 μl of 20% AcOH. It is measured in analogy with example 1e) and the standard curve shown in FIG. 7 is obtained.

EXAMPLE 8

In this example a process for the preparation of a reagent combination for determination of protein C and its use are described.

a) S-2366 (12 mg) is dissolved in 19.55 ml of distilled water and 0.45 ml of Protac ® C-solution (10 U/ml), Pentapharm, Switzerland) is added. Portions of 200 μl of the resulting solution are distributed on microcuvettes and freeze-dried according to example 1d).

b) Use of the reagent combination in determination of protein C.

Figure 9:
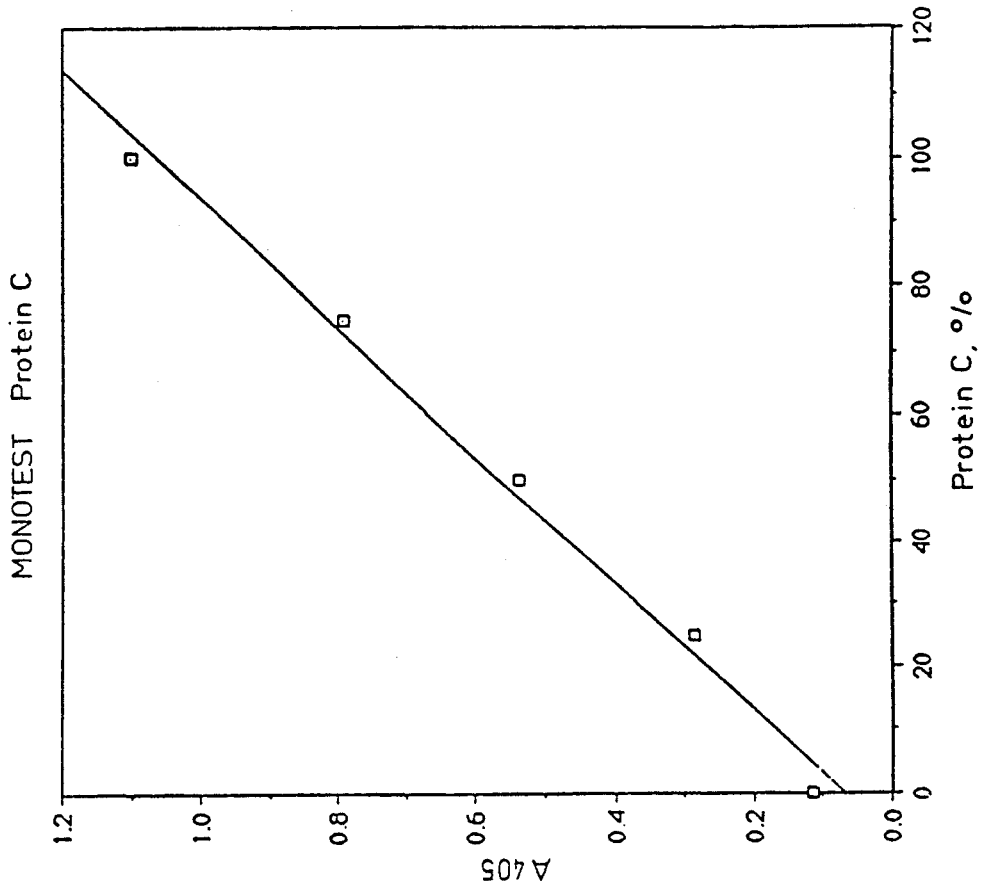
FIG. 9 illustrates a curve of absorbance at 405 nm for samples containing Protein C.
Figure 8:
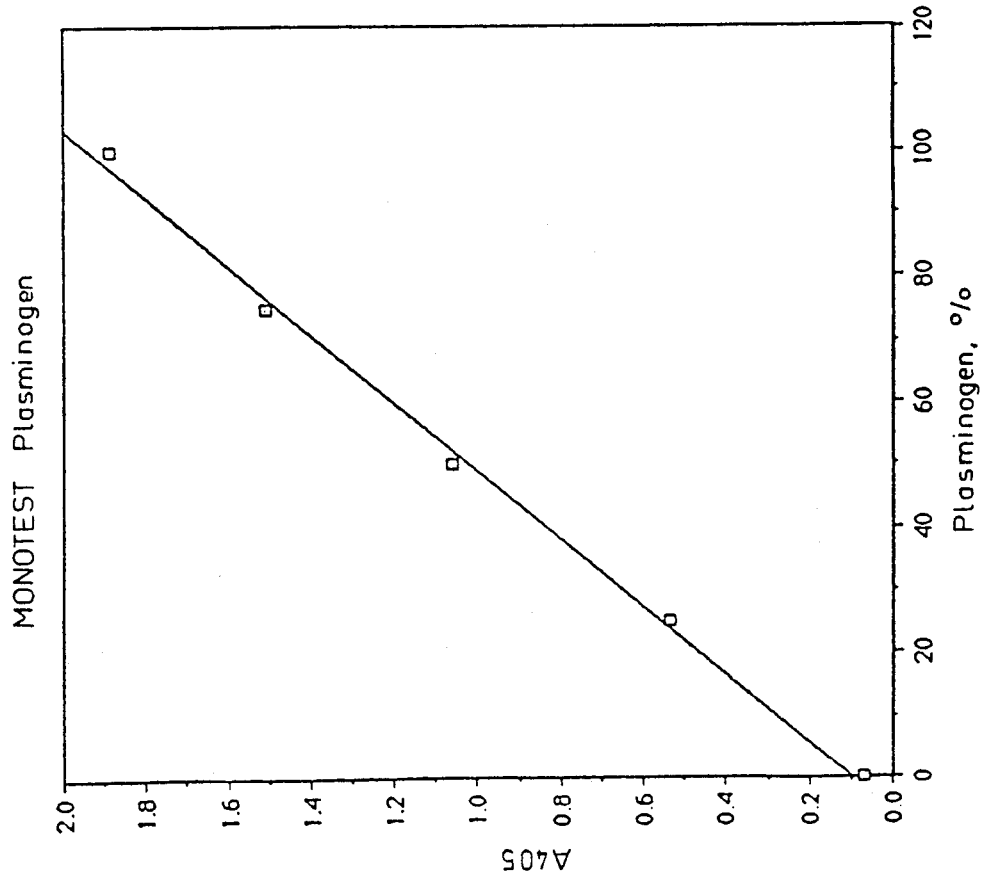
FIG. 8 illustrates a curve of absorbance at 405 nm for samples containing plasminogen.

300 μl plasma (diluted 1:11) in 0.025 mol/l Tris, pH=8.4 containing 0.1% PEG are added to the cuvette from a), the contents of which being freeze-dried and consisting of S-2366 (0.12 mg) and Protac ® C (0.045 U). The reaction is allowed to take place at 37° C. and is interrupted after 7 min through addition of 300 μl 20% AcOH. It is measured in analogy with example 1e) and the standard curve shown in FIG. 9 is obtained.

In these examples abbreviations have been used having the following meanings

| | |
|---|---|
| BSA | bovine serum albumin |
| Tris | tris(hydroxymethyl)-aminomethane |
| EDTA | ethylenediamine tetraacetic acid |
| PEG | Polyethylene glycol |
| AcOH | acetic acid |
| Tween ® 80 | polyoxyethylene sorbitan monooleate (Atlas Chemical Industries, U.S.A.) |
| Glu | glutamic acid |
| t-PA | plasminogen activator |
| S-2251 | H—D—Val—Leu—Lys-pNA.2HCl |
| S-2337 | Nα-benzoyl-Ile—Glu(γ-piperidide)-Gly—Arg-pNA.HCl |
| S-2366 | <Glu—Pro—Arg-pNA.HCl |
| S-2390 | H—D—Val—Phe—Lys-pNA.2HCl |
| S2732 | Nα-succinoyl-Ile—Glu(γ-piperidide)-Gly—Arg-pNA.HCl |
| pNA | p-nitroanilide |
| $A_{405}$ | absorbance at 405 nm |
| nkat | nanokatal (1 katal = the amount of enzyme activity that splits 1 mol substrate per sec. under specified conditions) |
| 1 U (Heparin) | unit related to international standard |
| 1 U (Streptokinase) | unit related to international standard |
| CU (plasminogen) | casein unit |
| U (Protac ®) | 1 U = the amount of Protac ® activating protein C included in 1 ml of normal human citrate plasma. |

The standard curves shown on the drawings have been obtained, preferably at the manufacturer of the reagent combinations, by measurement of $A_{405}$ for samples having varying known amounts of the component to be determined by means of the respective standard curve in analogy with the measurements carried out in the corresponding illustrative example.

We claim:

1. A dry reagent combination for the determination of a blood coagulation factor or a fibrinolysis factor, said combination comprising, in a substantially unreacted form and in an amount sufficient for a single test, a chromogenic substrate for a blood coagulation protease colyophilized with an enzymatically active component reactive with said substrate, and a buffer at pH, such that the enzymatically active component is inactive but not denatured;

wherein the component colyophilized with the substrate is a protease, and the factor to be determined is an inhibitor for the protease.

2. A kit comprising the reagent combination of claim 1 enclosed in a container having an undivided interior volume.

3. The dry reagent combination of claim 1 wherein the substrate is Nα-succinoyl-Ile-Glu(gamma-piperidide)-Gly-Arg-pNA and the component reactive with said substrate is Factor $X_a$, the factor to be determined being the inhibitor antifactor $X_a$ or the cofactor heparin.

4. The dry reagent combination of claim 3 wherein said combination comprises bovine serum albumin and mannitol colyophilized with the substrate and Factor $X_a$.

5. A process for the preparation of a reagent combination for the determination of an inhibitor for a protease, said process comprising the steps:
  (i) introducing into a container a sufficient amount for a single test of an aqueous solution of a chromogenic substrate and an enzymatically active component reactive with said substrate, said solution containing a buffer at a pH that provides non-denaturing conditions where said substrate and said active component are unreactive with each other, wherein said active component is a protease, and
  (ii) lyophilizing said solution while maintaining said unreactive conditions and said non-denaturing conditions.

6. The process of claim 5 wherein the lyophilization is carried out at 0.08–0.15 mbar at a temperature of −45° C. to −40° C. for 1–5 hours with a subsequent drying at a temperature of +12° C. to +24° C.

7. In an assay method for the determination of a blood coagulation factor or a fibrinolysis factor, said method comprising:
  (i) incubating in a single step a biological plasma sample with a chromogenic substrate for a protease, and an enzymatically active component reactive with said substrate, the incubation being performed in an aqueous solution providing the appropriate pH for the enzymatic degradation of the substrate, and
  (ii) measuring of the substrate degradation which is a measure of the amount of the coagulation or the fibrinolysis factor in the sample,
the improvement being adding the sample and an aqueous solvent that provides the appropriate pH-condition for the enzymatic substrate degradation to a colyophilized mixture comprising the substrate and the active component reactive with said substrate, and wherein the active component colyophilized with the substrate is a protease, and the factor to be determined is an inhibitor for the protease, and wherein a buffer is present at pH such that the enzymatically active component is inactive but not denatured.

8. The assay method of claim 7 wherein the substrate is Nα-succinoyl-Ile-Glu(gamma-piperidide)-Gly-Arg-pNA and the component reactive with said substrate is Factor $X_a$, the factor to be determined being the inhibitor antifactor $X_a$ or the cofactor heparin.

9. The assay method of claim 8 wherein said combination comprises bovine serum albumin and mannitol colyophilized with the substrate and Factor $X_a$.

10. The reagent combination of claim 1 wherein said protease is thrombin and said inhibitor is antithrombin.

11. The reagent combination of claim 1 wherein said protease is plasmin and said inhibitor is antiplasmin.

* * * * *